United States Patent
Levitsky et al.

(10) Patent No.: US 6,422,240 B1
(45) Date of Patent: Jul. 23, 2002

(54) ORAL/NASAL CANNULA

(75) Inventors: Gershon Levitsky; Joshua L. Colman; Sanford Brown, all of Jerusalem (IL)

(73) Assignee: Oridion Medical Ltd., Jerusalem (IL)

( * ) Notice: Subject to any disclaimer, the term of this patent is extended or adjusted under 35 U.S.C. 154(b) by 0 days.

(21) Appl. No.: 09/239,119

(22) Filed: Jan. 28, 1999

(51) Int. Cl.[7] .............................................. A61M 15/08
(52) U.S. Cl. .............................. 128/207.18; 128/207.14; 128/204.18
(58) Field of Search ..................... 128/207.18, 200.24, 128/204.18, 204.4, 204.12, 206.18, 207.13, DIG. 26, 912, 207.14; 604/94.01, 275, 533, 284

(56) References Cited

U.S. PATENT DOCUMENTS

| | | | |
|---|---|---|---|
| 759,152 A | * 5/1904 | Bennett ................. | 128/207.18 |
| 2,693,800 A | * 11/1954 | Caldwell ............... | 128/207.18 |
| 4,106,505 A | 8/1978 | Salter et al. | |
| 4,151,843 A | 5/1979 | Brekke et al. | |
| 4,156,426 A | 5/1979 | Gold | |
| 4,367,735 A | * 1/1983 | Dali ...................... | 128/207.18 |
| 5,046,491 A | 9/1991 | Derrick ................. | 128/200.24 |
| 5,375,593 A | * 12/1994 | Press ..................... | 128/207.18 |
| 5,495,848 A | * 3/1996 | Aylsworth et al. ..... | 128/207.18 |
| 5,740,799 A | * 4/1998 | Nielsen ................. | 128/207.18 |
| 5,794,619 A | * 8/1998 | Edelman et al. ....... | 128/207.18 |

FOREIGN PATENT DOCUMENTS

WO  WO 89/09565  10/1989

OTHER PUBLICATIONS

Woda, Russell P., et al., Cost–Benefit Analysis on Nasal Cannulae in Non–tracheally Intubated Subjects, Anesth Analg 1996, 82:506–510.
The Reliable Oral/Nasal ETCO2 Monitoring/o2 Delivering Device, A Medical Device Specifications Developer, Nasorcap Medspec. Inc., USA, 1993.

* cited by examiner

*Primary Examiner*—Glenn K. Dawson
(74) *Attorney, Agent, or Firm*—Hoffman, Wasson & Gitler (57) ABSTRACT

A nasal/oral cannula for the collection of exhaled gases from the nostrils of a patient, made up of two nasal prongs for insertion into the patient's nostrils and a collection tube for the collection of the exhaled gases, the nasal prongs and the collection tube being connected at a single junction, such that the exhaled gases flow freely from the nasal prongs to the collection tube. An oral prong can also be provided, whose end is placed near the oral cavity of the patient, the oral prong too being connected at the single junction of the nasal prongs and the collection tube.

23 Claims, 7 Drawing Sheets

ORAL/NASAL CANNULA

FIELD AND BACKGROUND OF THE INVENTION

The present invention relates to a nasal cannula and to an oral/nasal cannula, and, more particularly, to a nasal cannula and an oral/nasal cannula which permits both delivery of oxygen and accurate sampling of carbon dioxide.

For purposes of description, the discussion herein is focused on cannulas for use with human patients, it being understood that the present invention is not limited in scope only to use with patients and can beneficially be used in various other contexts.

Different types of oral/nasal cannulas are used to deliver oxygen to hospital patients who require assistance to breathe properly, to collect carbon dioxide samples from patients to monitor respiration, or to perform both functions. Such cannulas are used when direct ventilation is not provided. The term "oral/nasal" refers to the adaptable configuration of such cannulas which can be in close proximity to the oral cavity or inserted into the nasal cavity of the patient. In either arrangement, a sidestream of the patient's exhaled breath flows through the cannula to a gas analyzer to be analyzed. The results of this non-invasive analysis provide an indication of the patient's condition, such as the state of the patient's pulmonary perfusion, respiratory system and metabolism.

The accuracy of this non-invasive analysis of exhaled gases depends on the ability of a sampling system to move a gas sample from the patient to the gas analyzer while maintaining a smooth, laminar flow of gases, such that there are as few alterations to the waveform and response time of the concentration of the gases as possible. The waveform of the concentration of the gas is critical for accurate analysis. As the gas mixtures travels from the patient to the gas analyzer, the concentration of the gases can be affected by mixing of the component gases, which reduces the accuracy of the analysis of the sample by the gas analyzer, and reduces the amount of information obtained from that analysis.

Prior art nasal or oral/nasal cannulas unfortunately have caused significant alterations to these important features of the internal structure of the stream of exhaled gases. Such alterations have especially arisen as the result of attempts to combine the delivery of oxygen with the sampling of the exhaled breath of the patient. For example, the simplest nasal cannula design, consisting of a tube with two double hollow prongs for insertion into the nostrils, allows significant mixing of the oxygen which is delivered from the end of one tube, and the exhaled breath which is collected from the end of the second tube. Such mixing occurs when oxygen is delivered in a stream with strong force, so that the oxygen stream penetrates deeply into the nasal cavity even during expiration, thereby artifactually altering the composition of the exhaled gases.

However, attempts to prevent mixing between delivered oxygen and exhaled gases have resulted in other alterations to the exhaled gases. For example, one type of prior art nasal cannula (Salter Labs, Arvin, Calif. USA) consists of a tube with two openings at either end, and two hollow prongs projecting perpendicularly from the center of the tube with a partition between them. Oxygen enters the tube from one end and exhaled breath leaves the tube from the other end. The two hollow prongs are inserted into the nasal cavity of a patient, one prong in each nostril, so that oxygen could be delivered to, and exhaled breath collected from, the patient.

Unfortunately, the reliance of this cannula on a single nasal prong for collection of exhaled gases does not prevent the strong flow of delivered oxygen from the other nostril mixing with exhaled gases deep in the nasal cavity, above the nasal septum. Such mixing of delivered oxygen with exhaled gases reduces the accuracy of gas analysis.

In addition, this type of cannula usually has significant "void volume", or space in which mixing of gases and concurrent alteration of the gas waveform, can occur. Such space is often referred to as "void volume" because it is not part of the pathway for the flow of gases and hence is unproductive. For example, void volume arises in this cannula between the septum dividing the main tube and the junction of each prong with that tube. The presence of such void volume is a significant hindrance to the accurate analysis of exhaled gases. Thus, this prior art nasal cannula has a reduced efficiency for the collection of exhaled gases for analysis.

Another design for a nasal cannula (Hospitak, Lindenhurst, N.Y., USA) has two parallel overlapping tubes, one for delivering oxygen and one for receiving exhaled gases. The tube which receives exhaled gases has two nasal prongs, while the tube which delivers oxygen has two holes parallel to these prongs. Both tubes have two holes, such that the gases can flow freely from the prongs to the holes. This configuration allows delivered oxygen to easily mix with expired gases, even at the end of the expiration period, thereby reducing the accuracy of the gas analysis.

U.S. Pat. No. 5,046,491 discloses another type of nasal cannula which also includes a first tube with two double nasal prongs and a septum placed between the prongs. One prong delivers oxygen and the second prong collects exhaled gases. A second tube is attached to the first tube and has two holes which are placed in or near the oral cavity of the patient for collecting exhaled breath. One problem with this cannula is that the exhaled gases are collected through two outputs, which are then connected to two separate tubes. These separate tubes then join together before delivering the gases to the capnograph. If gases are not flowing at exactly the same rate through both tubes, for example due to condensation, then the waveform of the gas concentration is altered and the results of the analysis are affected. In addition, this cannula has significant void volume because of the large dimension of the tubes and because there are two outputs for collecting the exhaled gases. The large void volume also causes mixing of the gases. Thus, the cannula of U.S. Pat. No. 5,046,491 does not solve the prior art problems for accurate gas analysis by nasal cannulas.

Furthermore, none of these prior art cannulas is a true oral/nasal cannula, which can be placed in either the oral or nasal cavities of the patient interchangeably. Such prior art oral/nasal cannulas, which are described below in the "Description of the Preferred Embodiments", also have significant problems regarding the collection of gases for accurate analysis, but offer the desirable feature of flexibility concerning the respiratory cavity from which exhaled gases are collected. Patients often alternately exhale through the nasal cavity and the oral cavity. The advantage of the oral/nasal cannula is that exhaled gases can be automatically collected from either cavity. The disadvantage is that many prior art oral/nasal cannulas are susceptible to the intake of ambient air through that portion of the cannula which is not receiving exhaled air. For example, if the patient exhales through the oral cavity, ambient air can be sucked into the cannula through the opening provided for the nasal cavity. Such ambient air can dilute the concentration of gas in the exhaled breath of the patient, thus giving misleading results for the gas analysis.

Hereinafter, the term "respiratory cavity" refers to the oral cavity, the nasal cavity, or both cavities, of a patient.

In addition, the effectiveness of oxygen delivery by a cannula is determined by two principles, neither of which is completely fulfilled by prior art cannulas. The first principle is that the distribution of the delivered oxygen stream should be equal between the two nostrils of the patient. In most prior art cannulas, one nostril receives 1.2–2.0 times as much oxygen as the other. However, an equal distribution of oxygen is preferably for the following reasons. First, if one of the nostrils is blocked, the second will continue to deliver oxygen. Second, even flow rates for both nostrils will not cause the patient to feel excess pressure in one nostril, even at high flow rates for the delivered oxygen. Third, producing even flow rates through the presence of oxygen "clouds" near the nostrils of the patient will cause such "clouds" to be the same size at both nostrils, and will permit the more effective use of ambient oxygen present near the nostrils before the inspiration phase.

The second principle is that the oxygen stream should be delivered at a relatively slow rate, rather than being forced into the nostrils at a high rate, for the following reasons. First, an oxygen stream which is delivered at a slow rate will not penetrate deeply into the nostrils of the patient and so will not be collected during the exhalation phase, thereby preventing distortion of the carbon dioxide measurements because of dilution of the exhaled gases. Second, the patient will feel more comfortable since the oxygen stream will not be so forceful.

If both principles are fulfilled, then oxygen delivery and analysis of exhaled gases will be optimized. Unfortunately, many prior art cannulas fail to implement these principles and are thus lacking in this respect.

There is thus a widely recognized need for, and it would be highly advantageous to have, a cannula which does not alter the gas waveform, which does not easily become blocked or clogged, which has minimal added void volume, and which can deliver oxygen without disturbing the waveform of exhaled gases, yet which has the flexibility and adaptability of an oral/nasal cannula.

SUMMARY OF THE INVENTION

According to the present invention there is provided a nasal cannula for collection of exhaled gases from a patient having nostrils, comprising: (a) two nasal prongs for insertion into the nostrils of the patient; and (b) a collection tube for the collection of the exhaled gases from the patient, the nasal prongs and the collection tube being connected at a single junction, such that the exhaled gases flow freely from the nasal prongs to the collection tube. Preferably, the collection tube is a single collection tube. Also preferably, the nasal prongs are joined in an are substantially before being connected to the junction. Preferably, the collection tube delivers the exhaled gases to a capnograph for gas analysis.

According to another embodiment of the present invention, there is provided a cannula for collection of exhaled gases from a patient having nostrils and an oral cavity, including: (a) two nasal prongs for insertion into the nostrils of the patient; (b) an oral prong for being located proximately to the oral cavity of the patient; and (c) a collection tube for the collection of the exhaled gases from the patient, the nasal prongs, the oral prong and the collection tube being connected at a single junction located substantially near the nostrils of the patient, such that the exhaled gases flow freely from the nasal prongs and the oral prong to the collection tube. Preferably, the collection tube is a single collection tube. Also preferably, the oral prong features a distal portion, the distal portion being bent at an angle. More preferably, the angle is about 90 degrees, such that the distal portion is located proximately to the oral cavity of the patient. Most preferably, the distal portion features a cap, the cap being attached to the distal portion, and the cap being made of a substantially hydrophilic material, such that the cap absorbs condensation from the distal portion. Also preferably, the nasal prongs are joined in an arc substantially before being connected to the junction. Preferably, the collection tube delivers the exhaled gases to a capnograph for gas analysis.

According to preferred embodiments of the present invention, the cannula further includes (d) an oxygen tube for delivery of oxygen, the oxygen tube being located near the nostrils of the patient; and (e) two oxygen inlets connected to the oxygen tube and being disposed such that the oxygen flows from the oxygen tube into the nostrils of the patient.

Preferably, the oxygen tube is located either above or below the nostrils of the patient. Also preferably, the oxygen tube includes a centrally located input for receiving oxygen being placed substantially equidistant from both oxygen inlets. Preferably, the oxygen inlets are holes. More preferably, the holes have an first diameter at an inner surface of the oxygen tube and the holes have a second diameter at an outer surface of the oxygen tube, the first diameter being smaller than the second diameter. Most preferably, the oxygen tube features a screen, the screen being placed within the oxygen tube such that the oxygen flows from the oxygen tube through the screen. Preferably, the screen is constructed of a material selected from the group consisting of a hydrophobic porous material, a wide mesh and a netting.

Alternatively and preferably, the inlets are oxygen prongs for being inserted into the nostrils of the patient. More preferably, the oxygen prongs are substantially shorter in length than the nasal prongs, such that the nasal prongs extend farther into the nostrils than the oxygen prongs. Also more preferably, the oxygen prongs are formed of a substantially porous material, such that the oxygen prongs are permeable to gases. Most preferably, the oxygen prongs are formed from an inner cylinder and an outer cylinder, both cylinders being made from the substantially hydrophobic porous material, and the inner cylinder being substantially shorter in length than the outer cylinder.

According to other preferred embodiments of the present invention, at least a portion of the oxygen tube is formed from a substantially porous material such that the at least a portion of the oxygen tube is permeable to gases. More preferably, the at least a portion of the oxygen tube is located substantially between the oxygen prongs.

According to another embodiment of the present invention, there is provided a method of using the cannula of claim 1 for collecting the exhaled gases from the patient, including: (a) inserting the nasal prongs into the nostrils of the patient; (b) attaching the collection tube to a conduit for conducting gas; (c) connecting the conduit to a gas analyzer; and (d) applying a force at the gas analyzer, such that the exhaled gases flowing through the cannula moves from the collection tube to the gas analyzer.

According to yet another embodiment of the present invention, there is provided a cannula for collection of exhaled gases from a patient and for delivery of oxygen to a patient, the patient having nostrils and an oral cavity, including: (a) two nasal prongs for insertion into the nostrils of the patient; (b) an oral prong for being located proximately to the oral cavity of the patient; (c) a collection tube for the collection of the exhaled gases from the patient, the nasal prongs, the oral prong and the collection tube being connected at a single junction, such that the exhaled gases flow freely from the nasal prongs and the oral prong to the collection tube; (d) an oxygen tube for delivery of oxygen, the oxygen tube being located near the nostrils of the patient; and (e) two oxygen inlets connected to the oxygen tube and being disposed such that the oxygen flows from said oxygen tube into the nostrils of the patient.

Hereinafter, the term "attached" is defined as connected to, or integrally formed with. Hereinafter, the term "connected" is defined as communicating with. Hereinafter, the term "prong" refers to a hollow tube with two openings, one at each end of the tube.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is of a cannula which can effectively be used to collect samples of gas without reducing the accuracy of the analysis of the collected gas, and which is less likely to become blocked by condensed moisture, or by liquid or solid material, or their mixtures thereof, such as mucous or saliva. Specifically, the present invention has two prongs for insertion into the nostrils of a patient. These two prongs are joined outside the nasal cavity to a single output tube for collection of the exhaled gases. According to preferred embodiments of the present invention, a second tube is attached to the two prongs, which is parallel to the nasal prongs, for placement of the distal end of the tube near the oral cavity of the patient, thereby providing an oral/nasal cannula. According to other preferred embodiments of the present invention, an additional tube is provided for the delivery of oxygen, the additional tube having two additional prongs for insertion into the nostrils of the patient, and the additional tube being perpendicular to the additional nasal prongs.

The principles and operation of an airway adapter according to the present invention may be better understood with reference to the drawings and the accompanying description.

Figure 1:
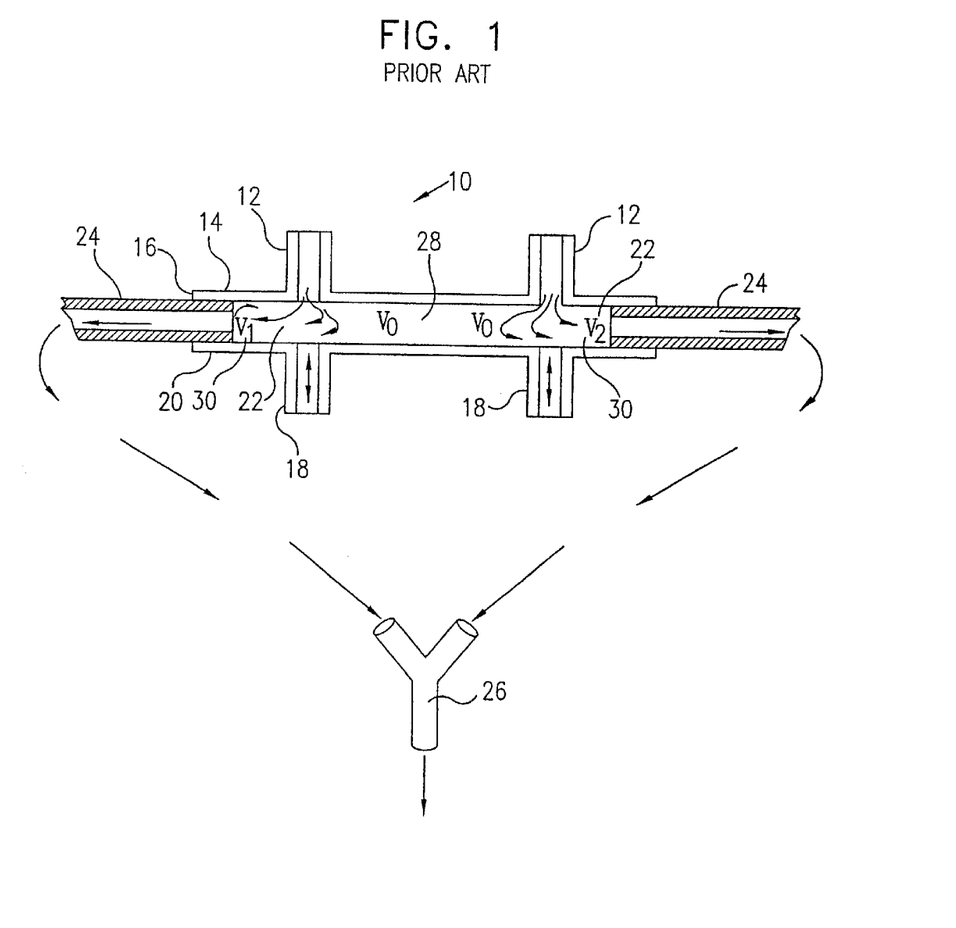
FIG. 1 is an illustrative prior art oral/nasal carbon dioxide cannula.

Referring now to the drawings, FIG. 1 shows a prior art oral/nasal carbon dioxide cannula. A cannula 10 has two nasal prongs 12 for insertion into the nostrils of a patient (not shown). Nasal prongs 12 are connected to a first side 14 of a hollow tube 16. Hollow tube 16 is substantially perpendicular to nasal prongs 12. Two oral prongs 18 are also connected to a second side 20 of tube 16 in a substantially perpendicular orientation, such that gas flow from nasal prongs 12 to oral prongs 18 through tube 16 is substantially free and unimpeded. Tube 16 also has two holes 22, one at each end of tube 16, for connection to one of a plurality of connectors 24. Each connector 24 is attached to a gas line (not shown) which is then connected to a Y-connector 26. Y-connector 26 is attached to a line which leads to a capnograph (not shown). Thus, cannula 10 is suitable only for collection of exhaled gases for analysis.

Prior art cannula 10 unfortunately has a significant void volume 28 (also designated as $V_o$) between nasal prongs 12, within which gases do not properly circulate. Two smaller void volumes 30 (also designated as $V_1$ and $V_2$) are also present parallel to nasal prongs 12 and oral prongs 18. Such void volumes 28 and 30. and especially the larger void volume 28, permit the mixing of exhaled gases from a currently exhaled breath with previously exhaled breaths, thereby increasing the response time, altering the waveform and introducing an artifact into the gas analysis. Furthermore, the separation of the exhaled gases into two streams from nasal prongs 12 by tube 16, the later reintegration of the two streams at Y-connector 26 and the subsequent great distance of about 0.5 m between tube 16 and Y-connector 26, also increases the response time if there is even a slight difference in the flow rate of the gases between tubes 16. Such separation potentially also results in two stream having different flow properties. For example, if one tube 16 accumulated more condensed water than the other, the corresponding stream of exhaled gases would have a lower flow rate, thereby altering the waveform of the gas concentrations and increasing the response time for gases in that tube 16. Thus, prior art cannula 10 cannot provide completely accurate collection of gases for analysis.

Figure 2:
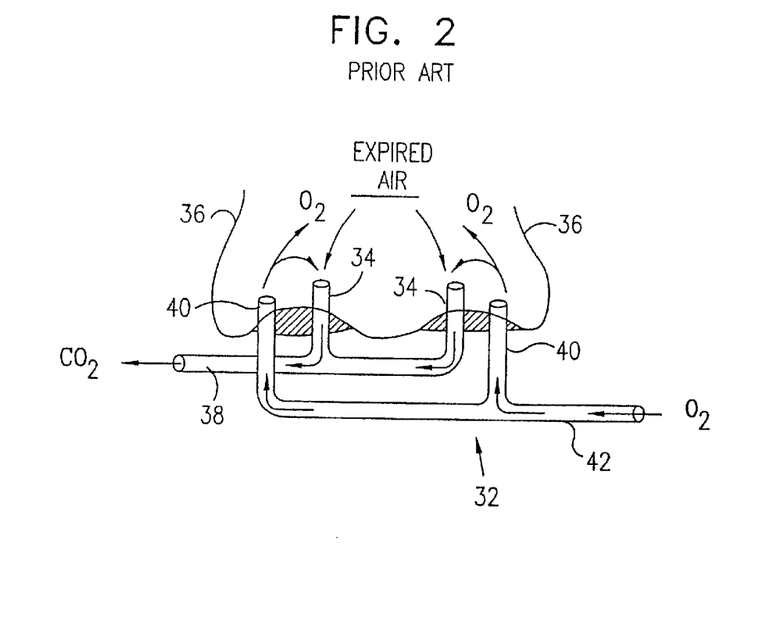
FIG. 2 is an illustrative prior art double nasal oxygen/carbon dioxide cannula for oxygen delivery and collection of exhaled gases.

FIG. 2 shows an exemplary prior art double oxygen/carbon dioxide nasal cannula for the collection of exhaled gases and the delivery of oxygen. A prior art nasal cannula 32 again has a first pair of nasal prongs 34 for insertion into nostrils 36 of a patient. First nasal prongs 34 are again connected to a first hollow tube 38. First hollow tube 38 is again substantially perpendicular to first nasal prongs 34. In addition, nasal cannula 32 has a second pair of nasal prongs 40 for insertion into nostrils 36. Second nasal prongs 40 are attached to a second hollow tube 42 in a substantially perpendicular orientation. First nasal prongs 34 and first hollow tube 38 are intended for the collection of exhaled gases from the patient, in a substantially similar configuration as that shown in FIG. 1. Second nasal prongs 40 and second hollow tube 42 are intended to deliver oxygen to the patient, so that nasal cannula 32 is capable of simultaneous oxygen delivery and gas collection.

Unfortunately, prior art nasal cannula 32 also permits the mixing of delivered oxygen and exhaled gases between first nasal prongs 34 and second nasal prongs 40 in nostrils 36, thereby diluting the true concentration of expired carbon dioxide. Thus, prior art nasal cannula 32 also introduces artifacts into the analysis of expired gases.

Also, the efficiency of oxygen delivery by prior art nasal cannula 32 is not sufficient because the oxygen flow rate varies between nasal prongs 40. Specifically, nasal prong 40 which is closer to the input of hollow tube 42 will have a higher flow rate than the other nasal prong 40. In addition, the strong oxygen stream into the nostrils creates discomfort for the patient, the alleviation of which is especially important for long term oxygen delivery.

Figure 3:
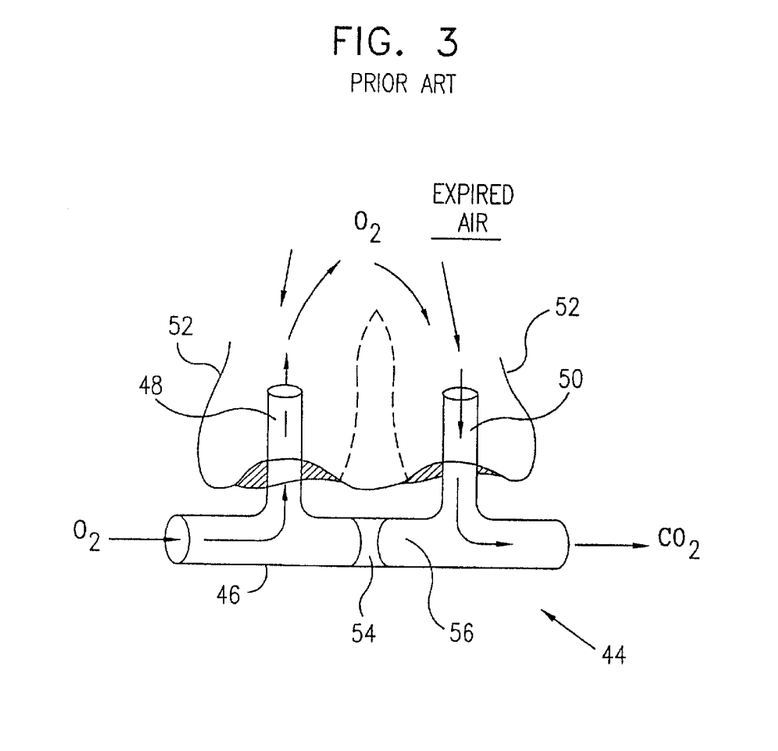
FIG. 3 is a second illustrative prior art divided nasal oxygen/carbon dioxide cannula for oxygen delivery and collection of exhaled gases.

FIG. 3 shows a second exemplary prior art divided oxygen/carbon dioxide nasal cannula for the simultaneous delivery of oxygen and collection of exhaled gases. A prior art nasal cannula 44 has a single tube 46 for both delivery of oxygen and collection of gases. Tube 46 has two nasal prongs 48 and 50 for insertion into nostrils 52 of a patient. Oxygen is delivered through nasal prong 48 and exhaled gases are collected from nasal prong 50. A septum 54 is present inside tube 46 between nasal prong 48 and nasal prong 50 to separate the delivered oxygen from the exhaled gases. However, particularly forceful streams of delivered oxygen can pass from nasal prong 48, penetrate deeply into nostrils 52, entering nasal prong 50 and dilute the true concentration of exhaled carbon dioxide. Furthermore, a significant void volume 56 is present between septum 54 and nasal prong 50, both increasing the response time and mixing the exhaled gases, which also reduce the accuracy of the analysis of the exhaled gases. Thus, prior art nasal cannula 44 is still not able to collect gases for a completely accurate analysis. In addition, the strong oxygen stream into the nostrils creates discomfort for the patient, the alleviation of which is especially important for long term oxygen delivery.

Figure 4:
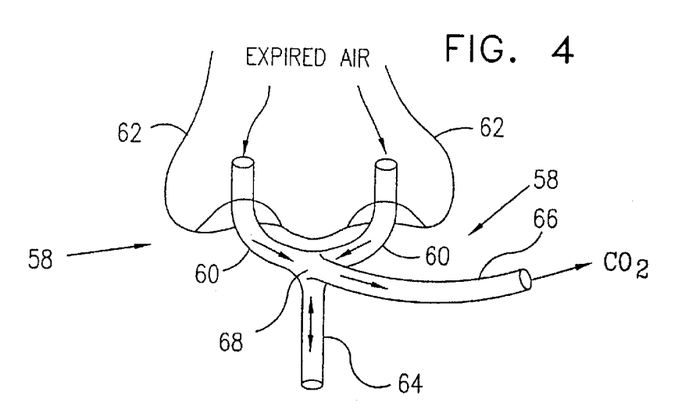
FIG. 4 is an illustrative oral/nasal cannula for the collection of exhaled gases according to the present invention.

FIG. 4 shows a schematic illustration of an exemplary novel oral/nasal carbon dioxide cannula for collection of exhaled gases according to the present invention. An oral/nasal cannula 58 also have a pair of nasal prongs 60 for insertion into the nostrils 62 of a patient. Cannula 58 preferably features an oral prong 64 for placement near the oral cavity of the patient (not shown) to form an oral/nasal cannula. If oral prong 64 is absent, then cannula 58 is a nasal cannula according to the present invention. Cannula 58 also has a collection tube 66 for collection of the exhaled gases for analysis by a capnograph (not shown). Nasal prongs 60, oral prong 64 and collection tube 66 meet at a single junction 68, which is preferably minimized to reduce void volume. Hereinafter, the term "single junction" refers to the joining of nasal prongs 60, oral prong 64 and collection tube 66 at least in close proximity, and preferably at exactly one junction.

At the very least, having the single junction 68 between all portions of oral/nasal cannula 58 significantly reduces the void volume, thereby reducing mixing of the gases and maintaining the response time. In addition, having the single collection tube 66, rather than two such tubes as in prior art cannulas, eliminates the division of the stream of exhaled gases as well as reducing the amount of void volume created.

Figure 5A:
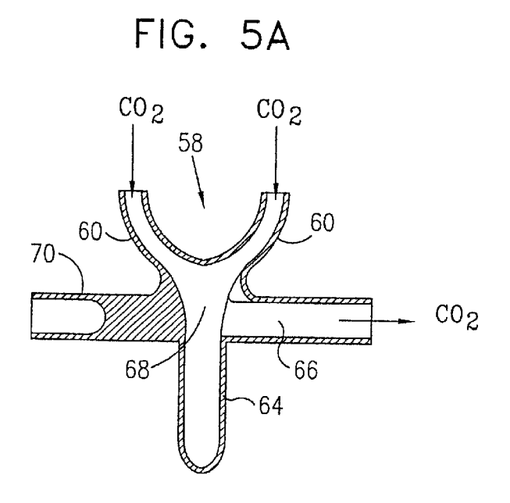
FIGS. 5A–5C are cross-sectional views of the cannula of FIG. 4 according to the present invention.
Figure 5B:
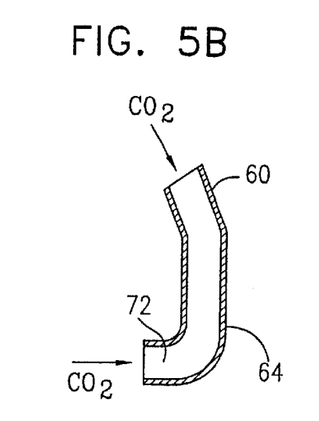
Figure 5C:
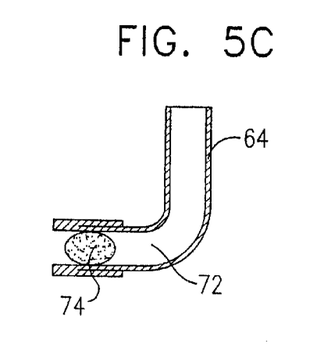

A cross-sectional view of the oral/nasal cannula of FIG. 4 is shown in FIGS. 5A–5C, clearly illustrating the small void volume created within the cannula. FIG. 5A shows a front cross-sectional view of oral/nasal cannula 58. As clearly shown in the illustration, nasal prongs 60, oral prong 64 and collection tube 66 all meet at a single small junction 68 with a minimum void volume. In practice, the void volume can be almost completely eliminated through this configuration, because there are no poorly ventilated areas within oral/nasal cannula 58. As shown in the illustration, a portion 70 of collection tube 66 does extend past nasal prongs 60 opposite to the collection point. However, portion 70 is blocked and is only intended to permit the attachment of a symmetrical loop which extends around the head of the patient (not shown).

FIG. 5B shows a side cross-sectional view of the connection between one nasal prong 60 and oral prong 64. Preferably, a distal end 72 of oral prong 64 is bent, more preferably at approximately a 90 degree angle from the remainder of oral prong 64, so as to be substantially parallel to the direction of flow of orally exhaled gases from the patient. Such an orientation both provides optimal response time for gas analysis and promotes self-clearing of condensation from oral/nasal cannula 58. Furthermore, preferably nasal prongs 60 are joined in an arc, so that condensation tends to move into oral prong 64 under dynamic pressure of the nasal exhalation of gases by the patient.

The structure of oral/nasal cannula 58 is designed to eliminate one significant problem with certain prior art oral/nasal cannulas, which is the susceptibility of these prior art cannulas to the intake of ambient air through that portion of the cannula which is not receiving exhaled air. For example, if the patient exhales through the nasal cavity, ambient air can be sucked into the prior art cannula through the opening provided for the nasal cavity. Such ambient air can dilute the concentration of gas in the exhaled breath of the patient, thus giving misleading results for the gas analysis. The structure of oral/nasal cannula 58 reduces or eliminates this problem with the presence of single small junction 68, and the bending of distal end 72 of oral prong 64. The resultant structure substantially prevents ambient air from entering the portion of cannula 58 which is not directly receiving exhaled air from the patient.

Also preferably, nasal prongs 60 and oral prong 64 have an optimal diameter, sufficiently large to promote rapid and easy removal of condensation from the interior of nasal cannula 58, yet not so large as to increase the response time. For this configuration, an optimal diameter for both nasal prongs 60 and oral prong 64 is in a range of from about 1.6 mm to about 2.0 mm.

Most preferably, distal end 72 of oral prong 64 features a porous, hydrophilic cap 74, as shown in cross-section in FIG. 5C. Porous hydrophilic cap 74 covers distal end 72 and absorbs water droplets formed from condensation which collects in nasal cannula 58. The particular advantage of cap 74 is that the material of cap 74 preferably attracts water away from oral prong 64, and then provides a relatively large surface area for evaporation of that water. Additionally, cap 74 relieves potential patient discomfort from water dripping from cannula 58 into the mouth of the patient.

Figure 6A:
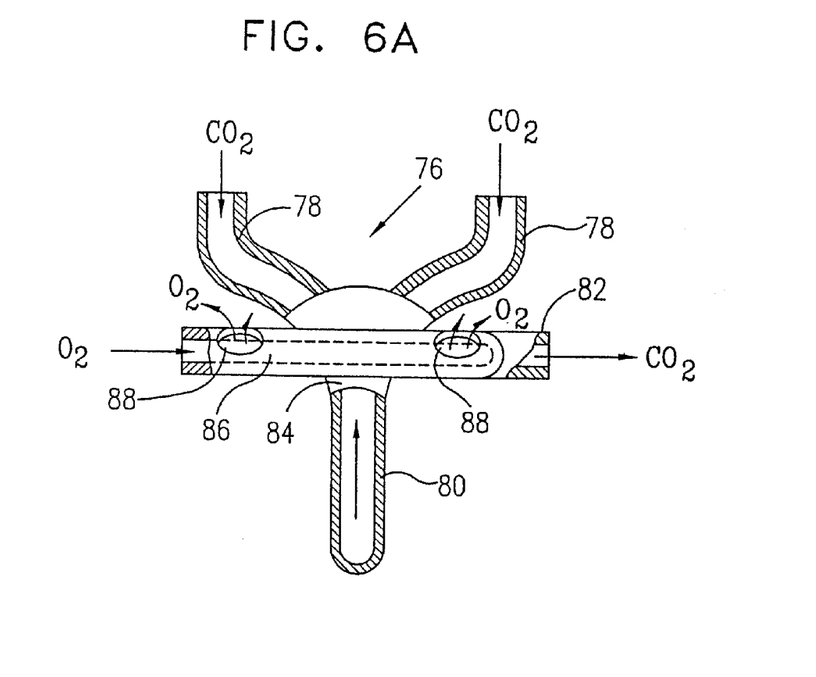
FIGS. 6A and 6B show cross-sectional views of a second illustrative embodiment of an oral/nasal cannula according to the present invention.
Figure 6B:
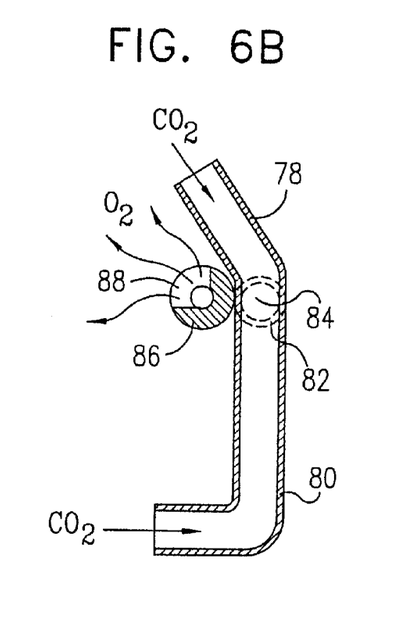
Figure 7A:
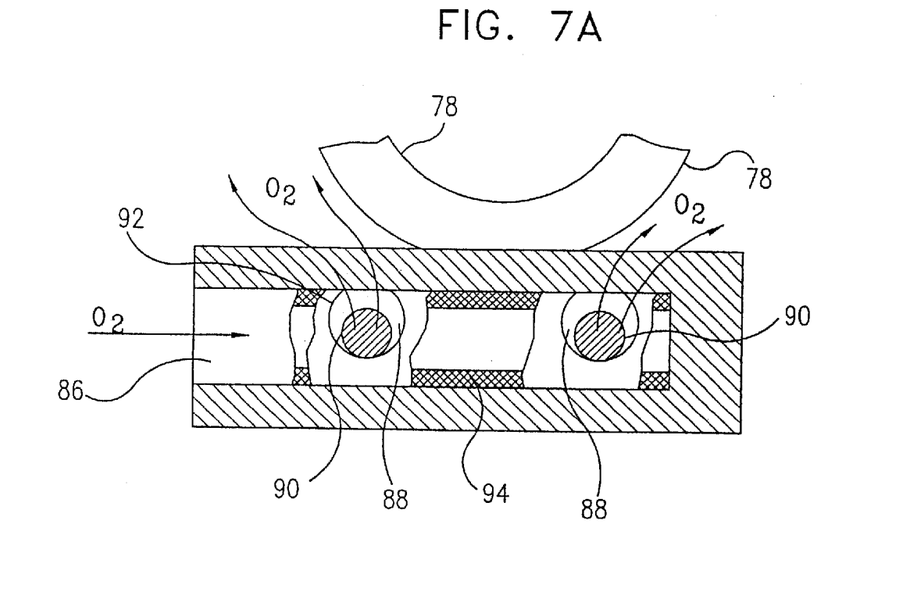
FIGS. 7A and 7B show portions of the oral/nasal cannula of FIGS. 6A and 6B in more detail, with the preferred addition of a porous screen to the oxygen tube according to the present invention.
Figure 7B:
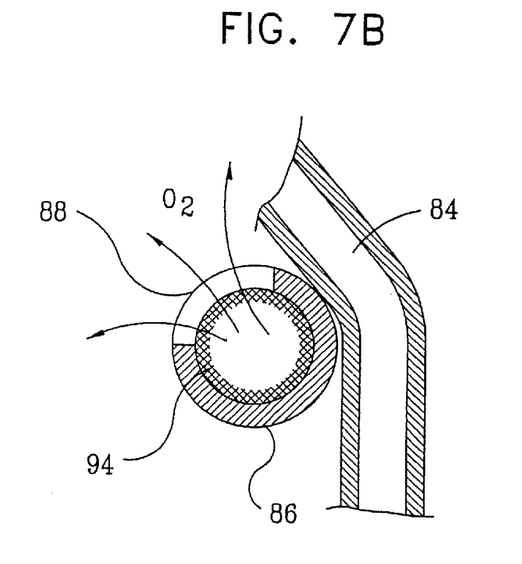

FIGS. 6A and 6B show cross-sectional views of a second preferred embodiment of the oral/nasal cannula for oxygen delivery and gas collection of the present invention. Detailed illustrations of portions of the cannula of FIGS. 6A and 6B are shown in FIGS. 7A and 7B. FIGS. 7A and 7B also show the preferred addition of a porous screen to the oxygen tube.

In this preferred embodiment, as shown in FIG. 6A, an oral/nasal cannula 76 again has a pair of nasal prongs 78 for insertion into the nostrils of a patient (not shown). Cannula 76 again preferably features an oral prong 80 for placement near the oral cavity of the patient (not shown) to form an oral/nasal cannula. Cannula 76 also has a collection tube 82 for collection of the exhaled gases for analysis by a capnograph (not shown). Nasal prongs 78, oral prong 80 and collection tube 82 again meet at a single junction 84, which is preferably minimized to reduce void volume.

Although cannula 76 also features an oxygen tube 86 for lying near the nostrils of the patient (not shown) and more preferably above or below the nostrils of the patient, substantially parallel with the upper lip of the patient (not shown), oxygen is not delivered through a second set of nasal prongs. Instead, oxygen tube 86 has two holes 88, through which oxygen is delivered to the patient. Holes 88 are placed near the nostrils of the patient yet do not enter the nostrils, thereby preventing the delivered oxygen from entering as a forceful stream of gases which dilutes the exhaled gases and reduces the accuracy of gas analysis.

FIG. 6B shows a side cross-sectional view of junction 84 between one nasal prong 78 and oral prong 80, as well as a portion of oxygen tube 86. Oxygen is shown being dispersed from oxygen tube 86 through hole 88.

FIG. 7A shows holes 88 in more detail. Holes 88 preferably have a relatively large diameter. Most preferably the diameter of holes 88 increases from the inner surface of oxygen tube 86 to the outer surface of oxygen tube 86, in order to reduce the force of the delivered oxygen stream. Holes 88 have a first smaller diameter 90 at the inner surface of oxygen tube 86, and a second larger diameter 92 at the outer surface of oxygen tube 86, with the diameter of holes 88 preferably gradually increasing from the inner to the outer surface of oxygen tube 86.

In addition, as shown in FIG. 7A, oxygen tube 86 preferably features a screen 94 made from a substantially porous material which is permeable to oxygen, such as a wide mesh, a hydrophobic porous screen, netting or cotton wool, for example. The advantages of screen 94 are that the force of the delivered oxygen stream is reduced and an oxygen "cloud" is created near the nostrils of the patient. The combination of the dispersion of oxygen through screen 94 and hole 88 is shown in a side, cross-sectional view in FIG. 7B, which also shows junction 84.

Figure 8A:
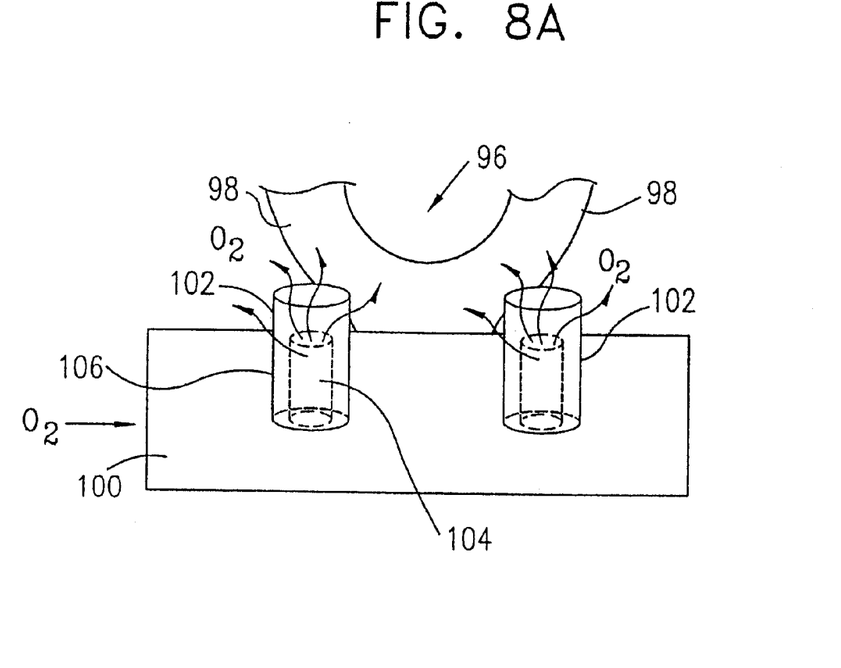
FIGS. 8A and 8B show detailed cross-sectional views of portions of a third embodiment of an oral/nasal cannula with porous oxygen delivery tubes according to the present invention.
Figure 8B:
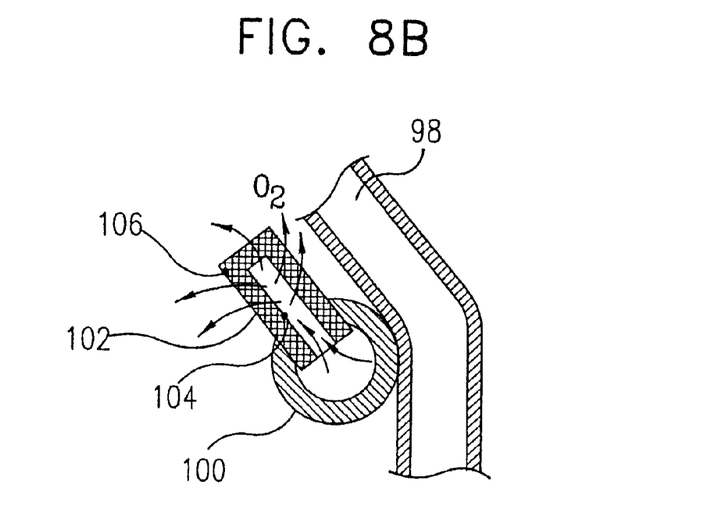

FIGS. 8A and 8B provide a detailed illustration of a portion of a third embodiment of an oral/nasal cannula according to the present invention. FIG. 8A shows a portion of an oral/nasal cannula 96, showing a section of a pair of nasal prongs 98 for receiving exhaled carbon dioxide, an oxygen tube 100 and a pair of second nasal prongs 102. As clearly illustrated, oxygen is delivered through oxygen tube 100 and is then dispersed through second nasal prongs 102.

Preferably, second nasal prongs 102 are constructed from two cylinders, in order to ensure that oxygen is delivered to the nostrils of the patient efficiently, yet is quickly dispersed within the nasal cavity. The first cylinder is an inner cylinder 104, preferably made from a substantially porous hydrophobic material. The material is preferably hydrophobic to prevent absorption of moisture. Inner cylinder 104 is surrounded by an outer cylinder 106, also preferably made from a substantially porous hydrophobic material, such that oxygen is dispersed throughout the nostrils of the patient, rather than entering the nasal cavity as a highly pressurized stream of gas.

FIG. 8B shows a side, cross-sectional view of the portion of the cannula illustrated in FIG. 8A. A junction 108 between one nasal prong 98 and an oral prong 110 is shown, as is one second nasal prong 102 with inner cylinder 104 and outer cylinder 106. The advantage of constructing second nasal prong 102 from a porous material is that such material would be permeable to oxygen, thereby allowing oxygen to disperse evenly from second nasal prong 102. Such dispersion reduces the force of the delivered oxygen stream.

Figure 9A:
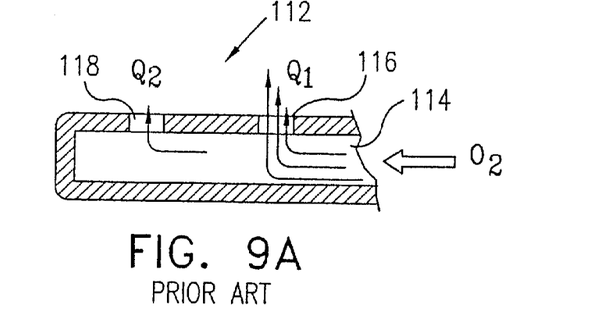
FIG. 9A shows a prior art cannula for oxygen delivery.
Figure 9B:
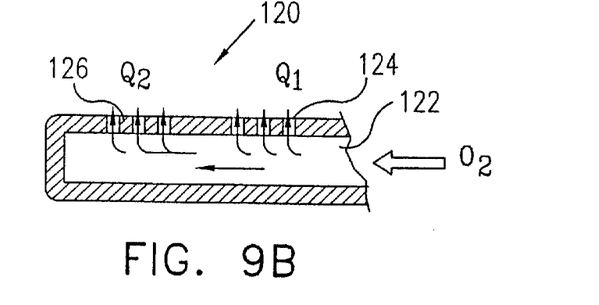
FIGS. 9B–9C show a cannula with equal oxygen delivery to each nostril according to the present invention.
Figure 9C:
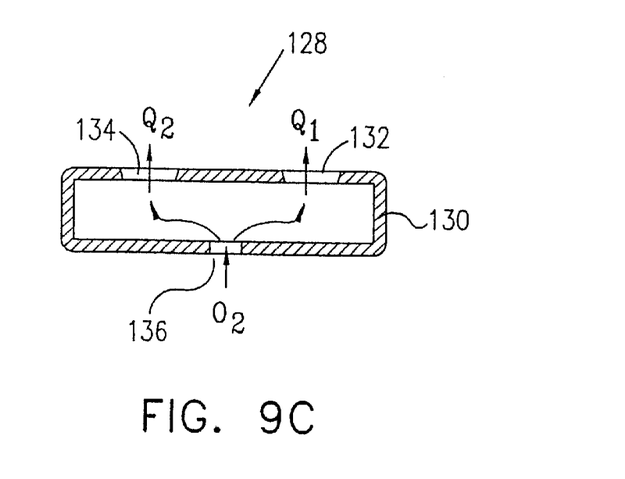

FIGS. 9A–9C show a comparison between a prior art oral/nasal cannula in which oxygen is delivered unequally to the nostrils of the patient (FIG. 9A), and a oral/nasal cannula according to the present invention in which oxygen is delivered at equal flow rates (FIGS. 9B and 9C). FIG. 9A shows a cross-sectional view of the oxygen-delivery portion of a typical prior art oral/nasal cannula 112. Prior art cannula 112 has an oxygen delivery tube 114 for delivery oxygen to two outputs 116 and 118. Outputs 116 and 118 could be holes or nasal prongs as shown previously. The problem with this configuration is that oxygen is not distributed evenly between both outputs 116 and 118. Output 116, which is closest to the start of oxygen delivery tube 114, has a greater flow of oxygen than output 118, as indicated by the arrows. Such a situation arises because of the resistance of outputs 116 and 118 to the flow of oxygen is much lower than the resistance of the connecting portion of oxygen delivery tube 114.

FIG. 9B shows a cross-sectional view of the oxygen-delivery portion of a first exemplary oral/nasal cannula 120 according to the present invention. First cannula 120 has an oxygen delivery tube 122 for delivery oxygen to two sets of outputs 124 and 126. Each set of outputs 124 and 126 includes at least two outputs, although three are shown here for illustrative purposes, without any intention of being limiting. Again, the outputs could be holes, with a porous screen, or nasal prongs as shown previously. The advantage of this configuration is that oxygen is distributed more evenly between both sets of outputs 124 and 126. Such a situation arises because the resistance of both sets of outputs 124 and 126 to the flow of oxygen is much greater than the resistance of the connecting portion of oxygen delivery tube 122.

FIG. 9C shows a cross-sectional view of the oxygen-delivery portion of a second exemplary oral/nasal cannula 128 according to the present invention. Second cannula 128 has an oxygen delivery tube 130 for delivery oxygen to two sets of outputs 132 and 134. Each set of outputs 132 and 134 includes at least one output, although only one is shown here for illustrative purposes, without any intention of being limiting. Again, the outputs could be holes, holes with a porous screen, or nasal prongs as shown previously. Additionally, oxygen delivery tube 130 features a centrally located input 136 for the delivery of oxygen. Preferably, centrally located input 136 is located substantially equidistantly to outputs 132 and 134. The advantage of this configuration is that oxygen is distributed more evenly between both sets of outputs 132 and 134 even for their relatively lower resistance to air flow in comparison to the resistance of oxygen delivery tube 130. Such a situation arises because the resistance of each output 132 and 134 to the flow of oxygen is equal.

TESTING OF THE ORAL/NASAL CANNULA

The features and embodiments illustrated herein may be better understood with reference to the experiments described below. These experiments were conducted on oral/nasal cannulas according to the present invention, as well as on examples of prior art cannulas.

Experimental Methods

The first test performed was the self-cleaning test. Self-cleaning is important for preventing the accumulation of condensed water, which can disturb the sampling of carbon dioxide. The term "$V_{ex}$" is defined as the minimal volume of expired breath required for self-cleaning of water from the cannula.

The second test was the response time test, performed in accordance with Regulation prEN 864:1992 (European Union standard) for capnography. All measurements were conducted on a capnograph with low flow rate of 47 ml/min. Response times (in mSec) were tested for nasal cannula blanks only, nasal cannula systems which also included the set of sample lines, and the entire capnograph set which included the nasal cannula system with a typical capnograph flow system.

The third test determined the accuracy of measurements of expired carbon dioxide ($EtCO_2$). Expired carbon dioxide was measured both with and without oxygen delivery. In the absence of oxygen delivery, the alteration to the true $EtCO_2$ caused by the influence of the response time was calculated as:

$\Delta (EtCO_2) = EtCO_2$ (True value) $- EtCO_2$ (with Entire Capnograph Set)

In the presence of oxygen delivery, the alteration to the true $EtCO_2$ was calculated as $\Delta (EtCO_2) = EtCO_2 (Q=0) - EtCO_2 (Q \neq 0)$ The fourth test measured the effectiveness of the delivery of oxygen according to the flow distribution between the two nasal cannula oxygen delivery outputs. Oxygen was delivered at the rate of 8 L/min. The flow of oxygen from each output, given as $Q_1$ and $Q_2$, was measured. The efficiency ($K_{eff}$) was determined according to the ratio of $Q_1$ to $Q_2$.

These four tests were performed on several different types of cannulas. Three types of cannulas were obtained and tested from Salter Labs (Arvin, Calif., USA): a nasal cannula (catalog number 4000); a dual oral/nasal cannula (catalog number 4001); and divided oxygen/carbon dioxide nasal cannula (catalog number 4707). Two types of cannulas were obtained and tested from Hudson (Temecula, Calif., USA): a nasal cannula (catalog number 1103); and an oxygen/carbon dioxide nasal cannula (catalog number 1843). An oral/nasal cannula according to the present invention was also tested, in the embodiment of an oxygen/carbon dioxide oral/nasal cannula with inserts of braid or cotton wool for oxygen dispersion as shown in FIG. 7B. Results for all tests are shown in Table 1.

Essentially, the cannula of the present invention performed at least as well as, any in many respects better than, the prior art cannulas. In particular, the cannulas of the present invention had a much lower response time than any of the other tested prior art cannulas. For example, without any additional connections, the cannulas of the present invention had a response time of 14, while those of the cannulas of Hudson were 97 and 47, and those of the cannulas of Salter Labs were 167, 143 and 239. Thus, clearly the cannula of the present invention had a far better response time than these tested cannulas.

While the invention has been described with respect to a limited number of embodiments, it will be appreciated that many variations, modifications and other applications of the invention may be made.

What is claimed is:

1. An oral/nasal cannula for collection of exhaled gases from a patient having nostrils and an oral cavity, comprising:
   two nasal prongs for insertion into the nostrils of the patient;
   an oral prong for placement near the oral cavity of the patient, said nasal prongs and said oral prong being connected at a junction configured to be located substantially near the nostrils of the patient; and
   a collection tube for the collection of the exhaled gases from the patient, said collection tube having two opposite ends, one of which is at said junction.

2. The cannula of claim 1, wherein said oral prong features a distal portion, said distal portion being bent at an angle such that it is directed towards the oral cavity of the patient.

3. The cannula of claim 2, wherein said distal portion features a cap, said cap being attached to said distal portion, and said cap being made of a substantially hydrophilic material, such that said cap absorbs condensation from said distal portion.

4. The cannula of claim 2, wherein said distal portion of said oral prong is bent at an angle such that it is substantially parallel to the orally exhaled air stream.

5. The cannula of claim 2, wherein said distal portion of said oral prong is bent at an angle such that when said patient exhales through his oral cavity, intake of ambient air through said nasal prongs is substantially prevented.

6. The cannula of claim 1, wherein said nasal prongs are joined in an arc substantially before being connected to said junction.

7. The cannula of claim 1, wherein said collection tube delivers said exhaled gases for gas analysis.

8. The cannula of claim 1, and further comprising:
   at least one oxygen tube for delivery of oxygen, said at least one oxygen tube being configured to be located near the nostrils of the patient; and
   two oxygen inlets connected to said at least one oxygen tube and being disposed such that said oxygen flows from said at least one oxygen tube through said oxygen inlets into the nostrils of the patient.

9. The cannula of claim 8 wherein said at least one oxygen tube includes a centrally located input, substantially equidistant from said two oxygen inlets for receiving oxygen.

10. The cannula of claim 8 wherein said at least one oxygen tube comprises two oxygen tubes, one disposed on each side of said two oxygen inlets.

11. The cannula of claim 8 wherein said oxygen inlets are holes.

12. The cannula of claim 11, wherein said holes include a screen constructed of a material selected from at least one of the group consisting of a hydrophobic porous material, a wide mesh, cotton wool, and a netting.

13. A nasal cannula for collection of exhaled gases from a patient having nostrils comprising:
   two nasal prongs for insertion into the nostrils of the patient, said nasal prongs being connected at a junction configured to be located substantially near the nostrils of the patient;
   a collection tube for the collection of the exhaled gases from the patient, said collection tube having two opposite ends, one of which is at said junction of said two nasal prongs.

14. The cannula of claim 13, wherein said at least one oxygen tube includes a centrally located input, substantially equidistant from said two oxygen inlets for receiving oxygen.

15. The cannula of claim 13 wherein said at least one oxygen tube comprises two oxygen tubes, one disposed on each side of said two oxygen inlets.

16. The cannula of claim 13, wherein said oxygen inlets are holes.

17. The cannula of claim 16, wherein said holes include a screen constructed of a material selected from at least one of the group consisting of a hydrophobic porous material, a wide mesh, cotton wool, and a netting.

18. A method of collecting exhaled gases from a patient having nostrils, the method comprising the steps of:

(a) providing a cannula featuring:

two nasal prongs for insertion into the nostrils of the patient said nasal prongs being connected at a junction configured to be located substantially near the nostrils of the patient; and a collection tube for collecting the exhaled gases from the patient, said collection tube having two opposite ends, one of which is at said junction of said two nasal prongs;

(b) inserting said nasal prongs into the nostrils of the patient;

(c) attaching said collection tube to a gas analyzer; and (d) applying a force at said gas analyzer, such that the exhaled gases flowing through the cannula move from said collection tube to said gas analyzer.

19. A method of collecting exhaled gases from a patient having nostrils and an oral cavity, the method comprising the steps of:

(a) providing a cannula featuring:

two nasal prongs for insertion into the nostrils of the patient;

an oral prong for placement near the oral cavity of the patient said nasal prongs and said oral prong being connected at a junction configured to be located substantially near the nostrils of the patient; and a collection tube for collecting the exhaled gases from the patient, said collection tube having two opposite ends, one of which is at said junction;

(b) inserting said nasal prongs into the nostrils of the patient;

(c) placing said oral prong near the oral cavity of the patient;

(d) attaching said collection tube to a gas analyzer; and (e) applying a force at said gas analyzer, such that the exhaled gases flowing through the cannula move from said collection tube to said gas analyzer.

20. A cannula for collection of exhaled gases from a patient and for delivery of oxygen to a patient having nostrils and an oral cavity, comprising:

(a) two nasal prongs for insertion into the nostrils of the patient;

(b) a collection tube for the collection of the exhaled gases from the patient, said nasal prongs and said collection tube being connected at a single junction, such that the exhaled gases flow freely from said nasal prongs to said collection tube;

(c) an oxygen tube for delivery of oxygen, said oxygen tube being configured to be located near the nostrils of the patient; and (d) two oxygen inlets connected to said oxygen tube and being disposed such that said oxygen flows from said oxygen tube into the nostrils of the patient.

21. The cannula of claim 20 and also comprising an oral prong for placement near the oral cavity of the patient, said oral prong also being connected at the single junction of said nasal prongs and said collection tube.

22. The cannula of claim 21, wherein said oxygen inlets are holes.

23. The cannula of claim 20, wherein said oxygen inlets are holes.

* * * * *

UNITED STATES PATENT AND TRADEMARK OFFICE
CERTIFICATE OF CORRECTION

PATENT NO.     : 6,422,240 B1
DATED          : July 23, 2002
INVENTOR(S)    : Gershon Levitsky It is certified that error appears in the above-identified patent and that said Letters Patent is hereby corrected as shown below:

<u>Title page,</u>
Insert Item, -- [30] Foreign Application Priority Data,
January 29, 1998      [IS]    Israel ……………………….. 123122 --

Signed and Sealed this

Twenty-fifth Day of November, 2003

JAMES E. ROGAN
*Director of the United States Patent and Trademark Office*